US007153887B1

(12) United States Patent
Birck et al.

(10) Patent No.: US 7,153,887 B1
(45) Date of Patent: Dec. 26, 2006

(54) USE OF 15-DEOXYSPERGUALIN FOR THE TREATMENT OF ANCA ASSOCIATED VASCULITIS

(75) Inventors: Rainer Birck, Mannheim (DE); Johannes Drexler, Kronberg (DE); Osamu Hotta, Sendai (JP); Rainer Nowack, Lindau (DE); Johannes Fokku van der Woude, Mannheim (DE)

(73) Assignees: Euro Nippon Kayaku GmbH, Frankfurt am Main (DE); Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/979,365

(22) PCT Filed: Apr. 14, 2000

(86) PCT No.: PCT/EP00/03430

§ 371 (c)(1),
(2), (4) Date: Mar. 28, 2002

(87) PCT Pub. No.: WO00/71103

PCT Pub. Date: Nov. 30, 2000

(30) Foreign Application Priority Data

May 25, 1999 (DE) ................................ 199 23 961

(51) Int. Cl.
*A61K 31/16* (2006.01)
*A61K 31/24* (2006.01)
(52) U.S. Cl. ..................................... 514/616; 514/634
(58) Field of Classification Search ................ 514/551, 514/616, 634, 540, 579
See application file for complete search history.

(56) References Cited

U.S. PATENT DOCUMENTS

| 5,250,442 | A | * | 10/1993 | Cabezas | ...................... | 436/509 |
| 5,624,938 | A | * | 4/1997 | Pernis | ......................... | 514/313 |
| 5,679,651 | A | * | 10/1997 | Richardson | ................... | 514/49 |
| 6,083,503 | A | * | 7/2000 | Lenardo | ................... | 424/184.1 |

FOREIGN PATENT DOCUMENTS

| DE | 197 11 803 A1 | 9/1998 |
| DE | 197 28 436 A1 | 1/1999 |
| EP | 0 673 646 B1 | 9/1995 |
| EP | 0 678 297 A1 | 10/1995 |
| WO | WO 99/03504 | 1/1999 |

OTHER PUBLICATIONS

"Immunosuppressive Effect of Deoxyspergualin in Proliferative Glomerulonephritis", Hotta et al., American Journal of Kidney Diseases, Nov. 1999, 34(5), 894-901.*

"Unique Action of an Immunosuppressive Agent, Deoxyspergualin, One Hematopoiesis in Mice", Memoto et al., Experimental Hematology, 1997, 25(13), 1339-1346.*

"Deoxyspergualin: A New Immunosuppressive Drug for the Treatment of Autoimmune Disease", Nikolic-Paterson et al., Nephron 1995, 70(4), 391-6.*

"Effect of 15-Deoxyspergulain on Graft-V-Host Disease in Mice", Nemoto et al., Transplant Proc., 1987, 19(5), 3985-6.*

Positive Results of Phase I Study Put LymphoStat-B on Fact Track for Drug Development, 2001, Lupus Foundation of America, Inc.*

"Multiple Sclerosis: An Autoimmune Disease of the Central Nervous System", Vandana Mathrani,2000 Third Web Report On Seredip.*

"Autoimmune Diseases Poorly Understood, Difficult to Treat", CNN.com, Jul. 4, 2000.*

"Tips for Getting a Proper Diagnosis of Autoimmune Disease", Infocus, Vo. 10, No. 2, Jun. 2002.*

"Autoimmune Diseases: Overview", The National Woment's Health Information Center, Oct. 2003, 2000.*

Okada et al, "Immunosuppressant Deoxyspergualin Induces Apoptotic Cell Death in Dividing Cells", Immunology 1998, pp. 370-376.

Schorlemmer et al, "Preclinical Studies with 15-Deoxyspergualin in Various Animal Models for Autoimmune Diseases", Animals of the New York Academy of Sciences, vol. 685, 1993, pp. 155-174, also referred to as XP 000974478.

Schorlemmer et al, "Curative Effects of 15-Deoxyspergualin on Murine Systemic Lupus Erythematosus-Like Disease in MRL/1 Autoimmune Mice", International Journal of Immunotherapy, vol. 7, No. 4, 1991, pp. 169-180, also referred to as XP 000974488.

Lebreton et al, "Structure-Immunosuppressive Activity Relationships of New Analogues of 15-Deoxyspergualin. 1. Stuctural Modifications of the Hydroxyglycine Moiety", Journal of Medicinal Chemistry, American Chemical Society, vol. 42, Jan. 28, 1996, pp. 277-290, also referred to as XP 000971394.

Schorlemmer et al, "Immunosuppressive Activity of 15-Deoxyspergualin (15-DOS) on Various Models of Rheumatoid Arthritis", Drugs under Experimental and clinical Research, vol. 17, No. 10/11, 1991, pp. 471-483, also referred to as XP 00097446.

Schorlemmer et al, "Immunosuppressive Therapy of Organ-Specific Nephritic Autoimmune Diseases with 15- Deoxyspergualin", Agents and Actions, vol. 39, 1993, pp. C121-C124, also referred to as XP 000974491.

(Continued)

*Primary Examiner*—Brian Kwon
(74) *Attorney, Agent, or Firm*—Frommer Lawrence & Haug LLP

(57) ABSTRACT

The invention describes the use of deoxyspergualin (DSG) or an analogue thereof for the preparation of a medicament for the treatment of and/or prophylaxis against hyperreactive inflammatory diseases and autoimmune diseases, wherein the treatment is performed in cycles.

32 Claims, 1 Drawing Sheet

OTHER PUBLICATIONS

Katayama, "Experimental Lung Transplantation in Rats: Antirejection Effects of FK506 and 15-Deoxyspergualin", MIE Medical Journal, vol. 40, No. 2, Aug. 1990, pp. 215-228, also referred to as XP 000974487.

Goral et al, "15 Deoxyspergualin Prolongs Survival During Acute Graft Versus Host Disease", Journal of Allergy and Clinical Immunology, vol. 99, No. 1, 1997, also referred to as XP 000957371.

Choi et al, "Immunomodulator Therapy in Inflammatory Bowel Disease", Digestive Diseases and Sciences, 1994, vol. 39, No. 9, also referred to as XP 000974490.

Birck et al, "15- Deoxyspergualin Induces Remission in Wegener's Granulomatosis: Report of Three Cases", Journal of the American Society of Nephrology, vol. 10, Sep. 1999, also referred to as XP 000974913.

Bumgardner et al, "New Immunosuppressive Agents", Gastroenterology Clinics of North America, vol. 22, No. 2, 1993, also referred to as XP 000974492.

Schorlemmer et al, "15 Deoxyspergualin _15-DOS) Has a Curative Effect on the Development of SLE-Like Autoimmune Disease in MRL/1Mice", Agents and Actions, vol. 34, No. 1/02, 1991, pp. 151-155, also referred to as XP 000974941.

Kalden et al, "Immunological Treatment of Autoimmune Diseases", Advances in Immunology, vol. 68, 1998, pp. 333-418, also referred to as XP 000974494.

Transplantation, vol. 51, p. 712-715, 1991.
Drugs Exp. Clin. Res., vol. 17, p. 471-483, 1991.
Drugs Exp. Clin. Res., vol. 17, p. 461-469, 1991.
Clin. Exp. Immunol., vol. 91, p. 232-236, 1993.
Scand. J. Immunol., vol. 36, p. 415-420, 1992.
J. Am. Soc. Nephrol., vol. 3, p. 1765-1774, 1993.
Clin. Exp. Immunol., vol. 95, p. 502-808, 1994.
Agents Actions, vol. 39, p. C121-C124, 1993.
Scand. J. Immunol., vol. 39, p. 333-336, 1994.
J. Neuro. Sci., vol. 112, p. 209-215, 1992.
Auotimmunity, vol. 8, p. 43-51, 1990.

* cited by examiner

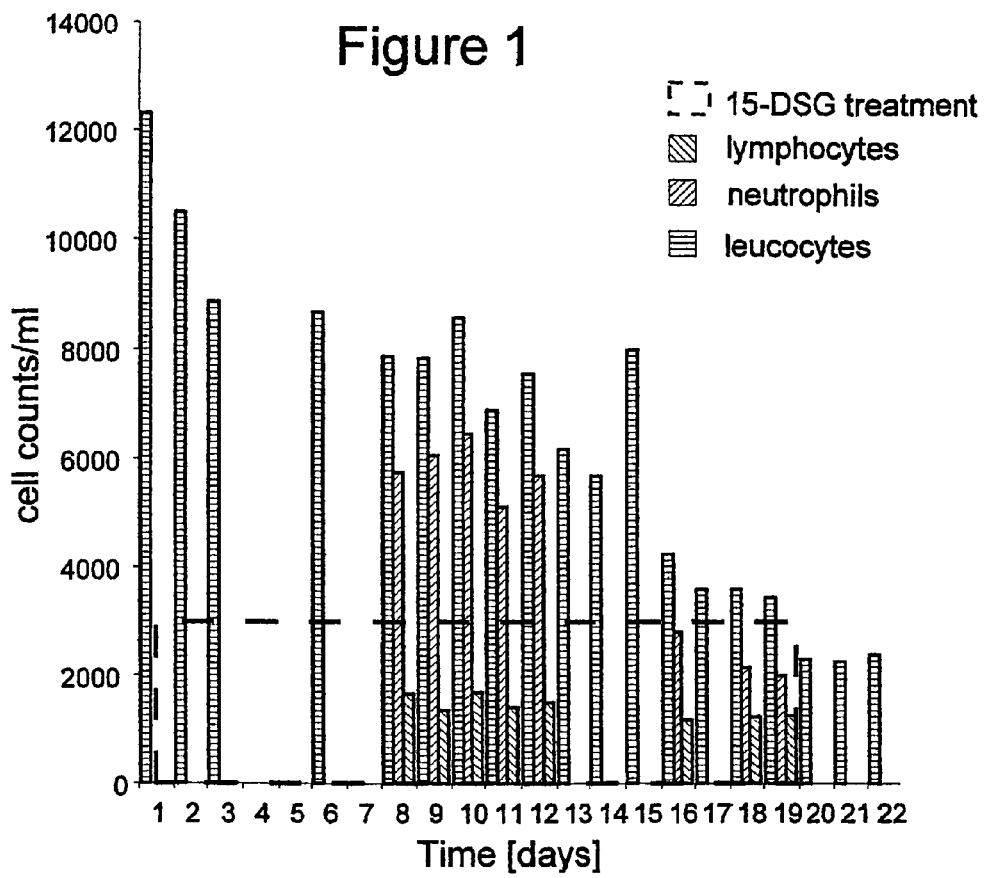
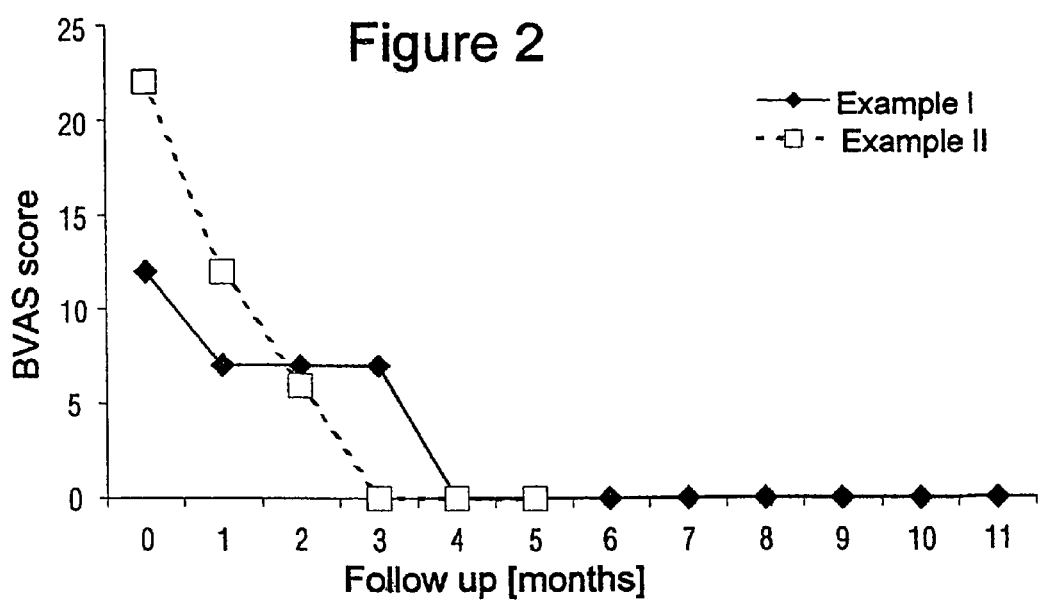

USE OF 15-DEOXYSPERGUALIN FOR THE TREATMENT OF ANCA ASSOCIATED VASCULITIS

The instant application is a 371 of PCT/EP00/03430, filed on Apr. 14, 2000, which claims priority to DE 199 23 961.4, filed on May 25, 1999.

The invention relates to the use of deoxyspergualin or analogues thereof for the preparation of a medicament for the treatment of hyperreactive inflammatory diseases, as vasculitis, and autoimmune diseases.

BACKGROUND OF THE INVENTION

Hyperreactive inflammatory diseases are characterized in that the body hyperreacts to nonspecific stimuli with an uncontrolled inflammation reaction. This inflammatory reaction (hyperreactivity) causes pathological changes leading to the onset of the disease and its chronic establishment. Concerning a definition and examples of hyperreactive inflammatory diseases reference is made to EP-0 673 646, explicitly incorporated herein. Vasculitis is an example of such a hyper-reactive inflammatory disease.

A general approach to vasculitis nomenclature and a set of definitions was agreed by consensus (Jennette et al., 1994, "Nomenclature of systemic vasculitides. Proposal of an international consensus conference" Arthritis and Rheumatism, 37, 187–92), and is incorporated herein by reference. According to this nomenclature, the distinction between the various forms of vasculitis depends principally on the size of vessel affected with recognition of charateristic features. Thus, the term vasculitis encompasses small vessel vasculitis (Wegener's granulomatosis, Churg-Strauss syndrome, microscopic poly-angiitis, Henoch-Schönlein purpura, essential cryoglobulin-aemic angiitis), medium-sized vessel vasculitis (cutaneous leucocytoclastic angiitis) and large vessel vasculitis (Poly-arteritis nodosa, Kawasaki's disease, Giant cell (temporal) arteritis, Takayasu's arteritis.). The salient features are illustrated in: "Oxford Textbook of Clinical Nephrology", 2nd edition (1998), Vol. 2, Chapter 4.5, incorporated herein by reference. See e.g. page 880, Table 1, for a short listing of the classification.

The clinical presentation of vasculitis is very diverse; it may be present as a primary disease or be associated with other diseases; vessels of different sizes may be affected in a single patient. The aetiology and pathogenesis are unknown in the vast majority of patients with vasculitis.

It was discovered that a certain spectrum of the diseases is associated with anti-neutrophil cytoplasmic antibodies, called ANCA. It is now clear that they are not only associated with Wegener's granulomatosis but also closely associated with microscopic polyangiitis and renal-limited vasculitis (i.e. isolated focal necrotizing glomerulonephritis), although these findings are more heterogenous than in Wegener's granulomatosis.

Autoimmune diseases are characterized by humoral, complement or cell-mediated immunity to constituents of the body's own tissues causing a clinical abnormality. As used herein, these tissues may also be allografts or xenografts, and graft-versus-host disease (GvHD) is considered an autoimmune disease for the purpose of this disclosure. Examples of autoimmune diseases are: collagenoses, vasculitides, arthritis, granulomatoses, organ specific autoimmunopathies as Morbus Crohn, ulcerative colitis and GvHD. In many diseases, autoimmune mechanisms are at least suspected as the molecular cause of disease. Various animal models of human autoimmune diseases exist and are used to test possible treatments. The diseases which may be treated according to the invention also encompass malignant diseases of the immune system as chronic immuno-proliferative syndrome, monoclonal gammopathies, Morbus Hodgkin and Non-Hodgkin-Lymphoma and chronic proliferative CD8-cell disease. The diseases which may be treated according to the invention generally encompass those mentioned in Peter/Pichler, "Klinische Immunologie", 2nd ed., Urban & Schwarzenberg, 1996, p. X–XIV (Teil C Klinik).

Therapies for many hyperreactive inflammatory diseases and autoimmune diseases have to be regarded as insufficient. In many instances this is due to severe side effects of the medicaments used. For example, for hyperreactive inflammatory diseases as Alzheimer's disease, pancreatitis and sepsis, there are no adequate treatments.

Regarding vasculitis, early attempts of treatment include the use of oral corticosteroids (OCS). Later, cyclophosphamid was added in steroid-resistant disease. A standard treatment of Wegener's granulomatosis, a form of vasculits, is a combination of cyclophosphamide (CYC) and oral corticosteroids (OCS). Various therapeutic regimen including Prednisolone and cyclophosphamide or Azathioprine are disclosed in "Oxford Textbook for Clinical Nephrology, pp. 890", referenced above.

However, those therapies suffer from several drawbacks, including a relatively high number of therapy-resistant cases, a considerable relapse rate and side effects. For example, long-term treatment with CYC carries the risk of serious drug-related morbidity and mortality. Also, in some patients even short-time exposure to cyclophosphamide leads to overt CYC-toxicity, e.g. marrow suppression, toxic hepatitis or haemorrhagic cystitis and secondary cancers.

Similarly, efficient therapies for autoimmune diseases involving little or no side effects are rare or, in most cases, absent.

Therefore, there is a continued need for improved treatments of hyperreactive inflammatory diseases and autoimmune diseases.

It was now unexpectedly found that 15-deoxyspergualin (DSG) or analogues thereof show a high efficiency in the treatment of hyperreactive inflammatory diseases and autoimmune diseases when the treatment is performed in treatment cycles.

DSG is a synthetic derivative of spergualin, a natural product isolated from *Bacillus laterosporus*. It was originally described as having antitumor activity, and subsequently was found to possess immunosuppressive properties in experimental transplantation. In additional studies, DSG has demonstrated immunosuppressive activity in many animal models of transplant rejection. For clinical human transplantation, the safety and effectiveness of DSG treatment were proved in kidney graft recipients. Moreover, DSG showed an immunosuppressive effect in animal models of autoimmune diseases (C. Odaka et al., Immunology, 95, 370–376, 1998) and hyperreactive inflammatory diseases (EP-0 673 646).

SUMMARY OF THE INVENTION

In accordance with one aspect of the present invention, a novel method for preventing, stabilising or causing the regression of hyperreactive inflammatory diseases, including vasculitis, and autoimmune diseases is disclosed. The method comprises the administration of a therapeutically effective amount of a component selected from the group consisting of 15-deoxyspergualin or its derivatives or analogues to a mammalian species in need of such treatment in two or more treament cycles.

As used herein, autoimmune diseases as defined above also encompass diseases in which the immunity is directed to constituents of tissues on allografts or xenografts, and, thus, graft-versus-host disease (GvHD). It also includes diseases in which autoimmune mechanisms are involved in the pathogenesis.

The term "hyperreactive inflammatory disease" is used as defined in EP-0 673 646, incorporated herein by reference. Vasculitis is an example of a hyperreactive inflammatory disease and is defined as indicated above and in the "Oxford Textbook of Clinical Nephrology", 1998, Chapter 4.5 (referenced above) and in: Jennette et al., 1994, "Nomenclature of systemic vasculitides. Proposal of an international consensus conference" Arthritis and Rheumatism, 37, 187–92, both explicitly incorporated herein by reference. Malignant diseases of the immune system (see Peter/Pichler, above, for examples) may also be treated according to the invention.

The phrase "preventing" a disease as used in the present application refers to partially or fully inhibiting the development or progression of disease.

The severeness and remission of the disease is defined primarily by clinical judgement. In addition, the severeness of vasculitis is commonly defined using the Birmingham Vasculitis Activity Score (BVAS) (Luqmani et al., Baillieres Clin. Rheumatol. (1997) 11(2):423–446).

BRIEF DESCRIPTION OF THE DRAWING

FIG. 1 shows the first treatment cycle and the levels of white blood cells (leucocytes), lymphocytes and neutrophils.
FIG. 2 shows the BVAS (Birmingham vasculitis activity score) during follow up.

DETAILED DESCRIPTION OF THE INVENTION

The methods of the present invention can be used for preventing, stabilizing or causing the regression of hyperreactive inflammatory diseases and autoimmune diseases.

In accordance with the present invention, various materials can be used in treating these diseases. Preferred materials include 15-deoxyspergualin (DSG) and analogues thereof. As used herein, "analogues" refers also to related compounds and derivatives of DSG and spergualin. Such compounds, which may be used in the present invention, are disclosed, inter alia, in EP-0 701 817, EP-0 669 316, EP-0 600 762, EP-0 212 606, EP-0 213 526, EP-0 347 820, EP-0 105 193, EP-0 241 797, EP-181 592, WO94/0414, WO96/24579, EP-0 743 300, EP-0 765 866, EP-0 349 297, WO 99/03504 and German Patent application No. 35 06 330.

In particular, but not exclusively, compounds characterized by the following formula (I) may be used:

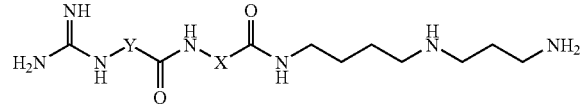

wherin Y is an alkylene group having an even number of from 4 to 12 carbons, preferably 6 to 10 carbons, or a meta or para mono-dialkylene phenyl radical substituent group, having in total 2 to 5 carbons in the alkylene residue (S), preferably 2 to 4 carbons, and X is an alkylene radical having 1 to 5 carbons, preferably 1 to 3 carbons, which may have hydroxy, methoxy or hydroxymethyl group at the alpha- or beta-position as a substituent, or NH—X—CO— is an amino acid residue, especially Gly, L-His, L- and D-Ser, gamma-ABA and DL-HABA.

Furthermore, preferred compounds are characterized by the formula (II):

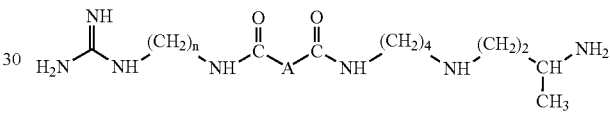

wherein: A is a single bond, —CH$_2$—, —CH$_2$—O—, —CH$_2$—NH—, —CH—(OH)—, —CHF— or —CH—(OCH$_3$)—; and n is 6 or 8.

Also preferred are compounds of the formula (III):

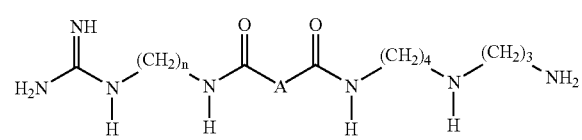

wherein: n is 6 or 8; A means a single bond, —CH$_2$—, —CH(OH)—, —CHF—, —CH—(OCH$_3$)—, —CH$_2$NH— or —CH$_2$—O— and its addition salts.

Two specific examples of useful derivatives of DSG are represented by formulae (IV) and (V), respectively:

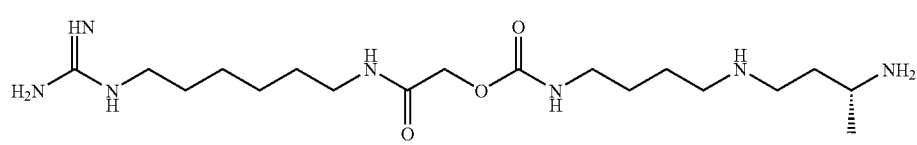

IV

-continued

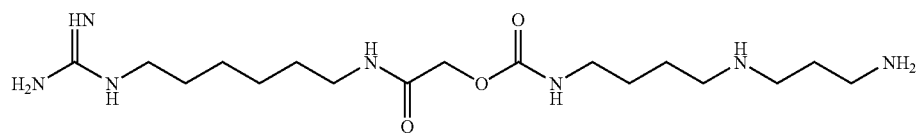

V 15-deoxyspergualin and the process for its preparation is described in U.S. Pat. Nos. 4,518,532 and 4,525,299 to Umezawa et al., while U.S. Pat. No. 4,851,446 to Umezawa et al., describes an immunosuppressing method comprising the administration of 15-deoxyspergualin and related compounds. The '299- and '466-patents are each incorporated herein by reference thereto.

According to a preferred embodiment of the present invention, DSG or an analogue or derivative thereof is administered subcutaneously. Thus, it was unexpectedly found that, in contrast to other immunosuppressants commonly used, DSG can be administered by subcutaneous injection without local complications and is efficient to reach a systemically effective concentration within short time. The feasability and effectivity of this mode of administration was even more surprising, as the information sheet on Gusperimus hydrochloride preparation (Spanidin) Inj. of Nippon Kayaku Co. Ltd., Japan, of April 1994, recommends an intravenous infusion over a time period of 3 hours.

According to the present invention, the treatment with DSG or an analogue thereof is performed in two or more treatment cycles. One treatment cycle is defined as a series of subsequent days of administration of DSG or its analogue. It is understood that the term "treatment cycle" as used herein also encompasses a series of subsequent administrations (at least two) wherein the time period between two subsequent administrations of the drug(s) is less than 24 hours or more than 24 hours, for example 48 hours, as long as these subsequent administrations form a treatment "block" or "cycle" which is separated from the next treatment cycle (block) by a time period which is considerably longer than the time period between two subsequent administrations within one treatment cycle. However, the latter time period is preferably less than 48 hours, in particular between 12 and 24 hours.

It has been surprisingly found that the sequence of treatment cycles interrupted by interphases in which no drug is administered is more efficient than a continuous administration (i.e. not in cycles). It is assumed, though the invention is not limited to a theoretical mechanism, that the multi-cycle treatment may provide a progressive immunomodulatory effect on the immune cell populations. This may be achieved by the repeated recovery (maturation and differentiation from progenitor cells) and selection of regulative or properly regulated cell populations. Cell populations directly or indirectly involved in the pathogenesis may be eliminated or otherwise inactivated during these repeated modulations.

According to a preferred embodiment of the present invention, a treatment cycle lasts at least for 5 days, preferably at least about 7 days, more preferably at least about 10 days, in particular at least about 14 days. The latter time period is preferred in order to make sure that all activated mature cells and all cells maturating during this time period are affected. According to a preferred embodiment, a treatment cycle lasts about 18 to 21 days, however, longer cycles may be used.

According to another preferred embodiment of the present invention, each cycle of treatment is aiming at a concentration of white blood cells of 3,000 to 4,000/µl in the peripheral blood. Thus, the white blood cell count of the patient is routinely determined and the decrease in white blood cells is monitored. As soon as the white blood cell count has dropped to the range from 1,000 to 5,000/µl, preferably from 2,500 to 5,000/µl, and in particular from 3,000 to 4,000/µl, the treatment is stopped to allow the concentration of white blood cells to recover to at least about the range from 4,000 to 8,000/µl.

It has been surprisingly found that the efficiency of the treatment may be also optimized by monitoring the level of granulocytes, and in particular neutrophils (in addition to or instead of white blood cells) in the peripheral blood of the patient and adjusting the duration of and interphase between the treatment cycles accordingly. Thus, according to another preferred embodiment of the present invention the neutrophil count of the patient is routinely determined and the decrease of neutrophils monitored. The numbers may be determined from a complete blood count (hemogram) of a blood sample, counting erythrocytes, leucocytes (WBC), thrombocytes and reticulocytes as well as from a differential blood count, performed by counting 100 nucleated cells in a blood smear. (A standard method may found in Pschyrembel, "Klinisches Wörterbuch", de Gruyter, p. 196 and 326.) When the level has dropped to the range from about 500 to about 4,000/µl blood, preferably from 1,000 to 4,000/µl blood, in particular from 2,000 to 3,000/µl blood, the cycle is terminated. The levels of peripheral blood lymphocytes (T- and B-cells) is also decreased, but to a lesser extent. The concentration of neutrophils is allowed to recover to at least about the range from 3,000 to 6,000/µl before the next cycle is started.

Thus, it was surprisingly found that the decrease and recovery in the number of whine blood cells, and particularly neutrophils, in the peripheral blood of the patients may be advantageously used as a parameter for optimisation of the cycle treatment. This correlation may indicate that these cell populations are directly or indirectly (via regulatory mechanisms) linked to the pathogenesis; however, this assumption does not limit the present invention.

It is noted that throughout the prior art literature, the leucocytopenia induced by DSG or analogues thereof has been described as an adverse side effect of the drug. In contrast, according to a preferred embodiment the present invention a controlled and defined decrease in leucocyte, and particularly in neutrophil counts, is even aimed at and made use of, as it has been surprisingly found that these parameters allow the optimisation of a multi-cycle treatment of hyper-reactive inflammatory diseases and autoimmune diseases.

It is known that the level of white blood cells and neutrophils, respectively, may vary from patient to patient. Thus, according to a preferred embodiment of the present invention, the duration and interval of the treatment cycles are monitored and determined in accordance with the percentual inhibition of white blood cells (WBC) or neutrophils, respectively. According to this preferred embodiment, a treatment cycle is aiming at a decrease (inhibition) of the WBC level of at least about 20%. (In other words, at the end of the cycle, only 80% or less of the WBC are left.) An inhibition of WBC of about 50 to about 80% is preferred. However, higher inhibition rates up to 95% or more may be used and may even be preferrable, as long as the remaining level of WBC is not critical to the patient. In other words, a severe decrease of WBC level is preferred, the lower limit being a WBC level which is still tolerable without causing health problems. Thus, the level of WBC (or neutrophils, see below) may be decreased to a WHO toxicity grade of 3–4 (corresponding to app. 1,000 WBC/µl or 500 neutrophils/µl).

Similarly, according to a preferred embodiment of the invention, the percentual inhibition of neutrophils is monitored in order to determine the duration and interval of the treatment cycles. Thus, a treatment cycle may be aiming at an inhibition of neutrophils in peripheral blood of at least 25%. A preferred inhibition rate is between 55% and 90%, however, higher inhibition rates may be used and even preferred. As stated above, the lower limit is determined by the minimum level of neutrophils tolerated without causing health problems to the patient (see above).

The preferred recovery of WBCs and neutrophils is as defined above (at least to about the range from 4,000 to 8,000 WBC/µl or at least about 3,000 to 6,000 neutrophils/µl).

According to a preferred embodiment, a dosage of at least 0.2 mg/kg body weight of the patient/day, preferably at least 0.3 mg/kg body weight of the patient/day may be advantageously used to induce a progressive and reproducible reduction of white blood cells in the patient within a reasonable cycle time. According to a further preferred embodiment a dosage of at least 0.5 mg DSG/kg body weight of the patient/day is used.

However, it may be preferable to use subcutaneous dosages of between 0.01 or 0.05 to 0.2 mg/kg body weight/day, especially in cases when such lower dosages lead to a better controllable and reasonably progressing decrease of WBCs/neutrophils.

According to an embodiment of the invention, the time period between two treatment cycles is between 4 to 20 days. However, in certain instances, depending on recovery of white blood cells and the other clinical parameters the time period between two treatment cycles may be shorter or considerably longer. Preferably, the interphase between two treatment cycles is between 10 days to five weeks, in particular between two and four weeks.

According to a preferred embodiment, the following protocol may be followed: in case the WBC count drops to 3,000/1 or less within less than 14 days, the cycle is terminated and the dosage of deoxyspergualin or its analogue is reduced in the subsequent treatment cycle (e.g. from 0.5 mg/kg/d to 0.25 mg/kg/d). In case the WBC count drops to 3,000/µl or less between day 14 and day 21 of the treatment cycle, the cycle is terminated and the subsequent treatment cycle is performed with an identical dosage. In case the WBC count has not dropped to 3,000/µl or less on day 21 of the cycle, the cycle is prolonged until such a WBC count is reached, maximally up to four weeks. The interval between two treatment cycles is generally about 14 days according to this embodiment. However, in case a relapse or increased disease activity occurs in the interval between two treatment cycles, the new treatment cycle may be started within less than 14 days from the termination of the previous cycle, under the proviso that a WBC count of at least 4,000/µl has been reached again.

According to an alternative embodiment, which may be preferred for life threatening cases and in patients suffering from a relapse or a severely increased activity of the disease, a dosage of about 5 mg/kg/d may be used intravenously (e.g. in a three hour slow infusion) until a WBC count of 3,000/µl or less is reached, or a maximum of 10 days. The treatment cycle is then followed by a rest until at least 4,000 WBC/µl are reached again. Preferably, the interval between two treatment cycles is around 14 days, unless a relapse occurs within the interval. The cycle treatment may be continued with a reduced dosage of spergualin or an analogue thereof as soon as disease control has been achieved.

According to one preferred aspect of the invention DSG or an analogue thereof are used in the treatment of vaculitis, in particular ANCA-associated vasculitis. It was found that the whole complex range of clinical symptoms associated with vasculitis could be improved and eliminated. Thus, it was surprisingly found that after 2 to 6 cycles of treatment with DSG or an analogue or derivative thereof a complete remission occured, since no acute or chronic disease activity was present. This is in contrast to the high relapse rate and incomplete remission observed with the standard therapy of cytotoxic agents combined with steroids, for example of cyclophosphamid and oral corticoids (OCS). Also, no toxic side effects occured in using DSG or an analogue or derivative thereof.

Thus, according to a preferred embodiment, the treatment comprises at least two, preferably at least three or four treatment cycles as set out above. In many cases it was found that typically 6 to 12 cycles are preferable.

According to another embodiment of the present invention, DSG or an analogue or derivative thereof is used in combination with other compounds known in the art to have a beneficial effect in the treatment of the disease treated. In the case of vasculitis, for example, oral corticosteroids (OCS) may be used. It was also found that when OCS are given concomittantly with the DSG treatment according to the present invention, the dose of OCS can be severly reduced, for example from 16 mg/d to about 6 mg/d (corresponding to about 0.02 to about 0.08 mg/kg body weight/d).

Similarily, in the case of various autoimmune diseases a combination with immunosuppressive drugs as corticosteroids may be used. The dosages commonly used are apparent to a person skilled in the art.

The deoxyspergualin compounds set forth above are typically used in the form of a pharmaceutically acceptable salt. Any salt of inorganic or organic acids may be used, as long as it is pharmacologically acceptable. Preferred examples include chloride or hydrochloride salts, especially the tri-hydrochloride salt. Examples of acceptable salts may be found in WO99/03504, incorporated herein by reference.

Though subcutaneous administration is preferred, any other mode of administration may also be used. Thus, the medicament may be prepared for a peroral, intravenous, intracutaneous, intraperitoneal, intrahecal, intraocular, ocular, buccal, nasal, percutaneous, cutaneous, topical, inhalative, intramuscular or rectal administration.

The clinically therapeutic dose of DSG and related compounds is from about 0,01 to about 100 mg/d/kg of patient body weight, preferably from 0,1 to 5 mg/d/kg, and may be administered in single or divided doses. For oral administrations up to 500 mg/d/kg may be used.

The present invention can also be practised using DSG and related compounds in a racemic mixture, as well as (+) and (−) isomers of DSG or its analogues.

In carrying out the methods of the present invention, the agent(s) used may be administered to humans, but also to other mammalian species, such as monkeys, dogs, cats, rats etc.

The agent used for treatment may be incorporated in a conventional dosage form, such as a tablet, capsule, elixier or injectable. The above dosage forms will also include the necessary carrier material, excipient, lubricant, buffer, antibacterial, bulking agent (such as mannitol), antioxidans (e.g. ascorbic acid or sodium bisulfite), or other necessary or beneficial additives as well-known or apparent to a person skilled in the art. Examples of excipients and carriers may be found in WO99/03504, incorporated herein by reference.

The following examples are further illustrative of the present invention. However, these examples are not intended to limit the scope of the present invention.

EXAMPLE I

A 35 year old male patient with Morbus Wegener had been suffering from progressive and relapsing disease despite various forms of immunosuppressive treatments for many years. The diagnosis of ANCA-associated systemic vasculitis was histologically confirmed. The patient showed severe involvement of the upper respiratory tract despite maintenance immunosuppression. He also showed subglottic stenosis necessitating trachystoma, glottic granulomata, saddle nose deformity, hoarseness, pansinusitis and otitis media sinistra with deafness. He had received almost all therapeutical standard options for treatment of vasculitis for which a beneficial effect has been described in the literature.

Thus, he had received cyclophosphamide (CYC) and OCS (oral corticosteroids), showing a toxic hepatitis after 4 weeks. The further treatment history had included Azathioprene (AZA), Mycophenolate Mofetil (MMF), ATG (anti-thymocyte-globuline), MTX (Methotrexate), IVG (intravenous immunoglobulins) and plasmapheresis, showing several relapses. The disease activity according to the BVAS before DSG-treatment was 12.

The DSG used was a Gusperimus hydrochloride preparation (100 mg/vial) (Spanidin inj.) of Nippon Kayaku Co. Ltd., Tokyo, Japan. The formulation also contained 200 mg of lactose as an inactive ingredient. The lyophilized DSG (100 mg) was reconstituted with physiological saline and admininstered at 0,5 mg/kg/d subcutaneously over 19 days. During this treatment cycle, the white blood cell count in peripheral blood dropped from 12,300 white blood cells (WBC)/µl on day 1 to 3,460 WBC/µl on day 19. Treatment with DSG was discontinued and white blood cell counts recovered to 9,600/µl on day 33. No side effects were observed. The levels of white blood cells and neutrophils were regularity monitored. It was observed that those levels reached a nadir a few days after termination of a treatment cycle and then recovered in an almost predictable manner.

The second DSG-treatment cycle was started on day 33 and subcutaneous administration of DSG was continued until day 52 (WBC count 3,500/µl). Following an treatment rest from day 52 to day 65 (WBC count 11,500/µl), a third treatment cycle was performed from day 66 to day 85 (WBC counts 12,000/µl and 3,800/µl, respectively).

Neutrophil counts were always in the range from 2,000/µl to 3000/µl at the termination of a cycle and above 4,000/µl when the subsequent cycle was started.

The first treatment cycle and the levels of white blood cells (leucocytes), lymphocytes and neutrophils are shown in FIG. 1. The shaded area corresponds to the first cycle (DSG administration period).

The BVAS (Birmingham vasculitis activity score) during follow-up is shown in FIG. 2.

After the first two treatment cycles with DSG the patient experienced a significant improvement of his clinical condition.

After the third cycle, complete remission occured as determined by clinical judgement and BVAS (=0). Moreover, it was possible to taper steroids from initially 16 mg methylprednisolone (corresponding to about 0.2 mg/kg body weight) to 6 mg (corresponding to about 0.08 mg/kg body weight). During all treatment cycles, no adverse side effects of DSG have been observed and the drug was well tolerated. This has not been possible in the past without provoking relapses.

In conclusion, this Example shows that the cycle treatment with DSG was very effective even in this therapeutically difficult patient.

EXAMPLE II

A 50 year old female with M. Wegener having ANCA-associated systemic vasculitis showed involvement of peripheral nerves, kidney, gut and eyes. The diagnosis of ANCA-associated systemic vasculitis was confirmed histologically and immunologically.

The patient showed mononeuritis multiplex with palsies, necrotizing glomerulonephritis, stenosis of small bowel segments, sinusitis, serotympanon and episcleritis. She had also been given various treatments including CYC+OCS, AZA and MMF with frequent relapses.

Therefore, DSG was administered subcutaneously as described in Example I (0,5 mg/kg/d).

The two treatment cycles were 14 days and 21 days, respectively, and were terminated at white blood cell counts in the range of 3,000–4,000/µl (neutrophil counts (2,000–3,000/µl). The levels of white blood cells and neutrophils were regularly monitored. Treatment cycles were started at white blood cell counts above 4,000/µl, and neutrophil counts above 3,500/µl.

A complete remission was observed even after two treatment cycles (BVAS=0.), starting from an initial BVAS of 19.

The BVAS (Birmingham vasculitis activity score) during follow up is shown in FIG. 2.

EXAMPLE III

MRL/lpr mice develop systemic lupus erythematosus (SLE)-like lesions. The disease is characterized by massive lymphadenopathy, development of antibodies to self antigens, and glomerulonephritis. Therefore, these mice offer a good model for autoimmune disease.

Male MRL/MpJ-lpr/lpr (MRL/lpr) mice were obtained from Charles River Japan (Atsugi, Kanagawa, Japan). The mice were maintained in specific pathogen-free conditions.

DSG was obtained and prepared as described in Example I.

DSG was administered from week 13 through week 20 (58 days):

(A) i.v. at daily doses of 1.5 mg/kg or (B) in three treatment cycles of 10 days with 1.5 mg/kg DSG i.v. daily with an interphase (no DSG) of 14 days after the first and second cycle.

Each treatment group (A and B) consisted of 10 mice. A set of control MRL/lpr-mice (10) receiving saline were included.

At the end of the experiment (day 59), the weight of the lymph nodes, serum anti-DNA titer and BUN (blood urea nitrogen) were measured as described by Nemoto, K. et al., J. Antibiotics, (1990), 1590–1591. The levels of white blood cells in peripheral blood were decreased both in groups A and B to about 6,000/µl compared to about 18,000/µl in the control group.

However, the mice of group B, treated according to the invention, showed a more pronounced reduction of weight of the mesenteric, axillary, elbow, inguinal, submaxillary and iliac lymph nodes as compared to group A. Also, the BUN and the anti-DNA titer was at a significantly lower level in group B as compared to group A.

Thus, the cycle treatment with DSG according to the invention in the early phase of the autoimmune disease was superior to continuous daily administration of an equal dosage of DSG and was more efficient in suppressing the development of SLE-like lesions. This was even more surprising, as the total amount of DSG administered in group B was almost half of that administered in group A.

The invention claimed is:

1. A method of treating anti-neutrophil cytoplasmic antibodies (ANCA) associated vasculitis in a patient resistant to corticosteroid treatment and at least one agent selected from the group consisting of cyclosphosphamide, azathioprine, mycophenolate mofetil, anti-thymocyte-globuline, methotrexate and immunoglobulin which comprises administering an effective amount of medicament comprising 15-deoxyspergualin or a pharmaceutically acceptable salt to said patient to treat said ANCA associated vasculitis, wherein said administration is performed in at least two treatment cycles and an interphase in which no drug is administered between the cycles; wherein each treatment cycle lasts from about 5 days to about 21 days; and wherein the interphase lasts from 10 days to 5 weeks.

2. The method according to claim 1, wherein the medicament comprising 15-deoxyspergulain or a pharmaceutically acceptable salt is administered subcutaneously.

3. The method according to claim 1, wherein, at the conclusion of a treatment cycle, the patient has a level of white blood cells (WBC) in peripheral blood of the patient which is in a range from about 1,000 to about 5,000/µl of blood.

4. The method according to claim 3, wherein the range is from about 2,000 to about 5,000/µl of blood.

5. The method according to claim 3, wherein the range is from about 3,000 to about 4,000/µl of blood.

6. The method according to claim 1, wherein, at the conclusion of a treatment cycle, the patient has a level of neutrophils in the peripheral blood of patient which is in the range is from about 500 to about 4,000/µl of blood.

7. The method according to claim 6, wherein the range is from about 1,000 to about 4,000/µl of blood.

8. The method according to claim 6, wherein the range is from about 2,000 to about 3,000/µl of blood.

9. The method according to claim 3, wherein the next treatment cycle is started when the level of white blood cells in peripheral blood of the patient is recovered to at least about 4,000/µl of blood.

10. The method according to claim 6, wherein the next treatment cycle is started when the level of neutrophils in peripheral blood of the patient is recovered to at least about 3,000/µl of blood.

11. The method according to claim 1, wherein, at the conclusion of each treatment cycle, the patient exhibits a decrease of WBC in peripheral blood of the patient of at least about 20%.

12. The method according to claim 11, wherein the decrease is at least 50%.

13. The method according to claim 11, wherein the decrease is at least 80%.

14. The method according to claim 1, wherein at the conclusion of each treatment cycle, the patient exhibits a decrease of netrophphilis in peripheral blood of the patient of at least 25%.

15. The method according to claim 14, wherein the decrease is at least 50%.

16. The method according to claim 14, wherein the decrease is at least 90%.

17. The method according to claim 1, wherein the interphase between at least two of the treatment cycles is from two to four weeks.

18. The method according to claim 1, wherein the interphase between at least two of the treatment cycles is about 14 days.

19. The method according to claim 1, wherein, in case a relapse or increased disease activity occurs in the interval between two treatment cycles, the new treatment cycle is started within less than 14 days from the termination of the previous cycle with proviso that a WBC level in peripheral blood of at least 4,000/µl of blood is reached again.

20. The method according to claim 1, wherein at least 3 or 4 treatment cycles are performed.

21. The method according to claim 1, wherein a treatment cycle is terminated when the patient has a level of WBC in peripheral blood of 3,000/µl of blood or less within 14 days from the start of the treatment cycle and the amount of 15-deoxyspergulain or a pharmaceutically acceptable salt is reduced in the subsequent treatment cycle.

22. The method according to claim 1, wherein a treatment cycle is terminated when the patient has a level of WBC in peripheral blood of 3,000/µl of blood or less between 14 days and 21 days from the start of the treatment cycle and the amount of 15-deoxyspergulain or a pharmaceutically acceptable salt in the medicament is identical in the subsequent treatment cycle.

23. The method according to claim 1, wherein the medicament is administered intravenously in an amount such that about 5 mg/kg/d of 15-deoxyspergulain or a pharmaceutically acceptable salt is administered to the patient until either (i) a WBC level in peripheral blood of 3,000/µl of blood or less is reached or (ii) 10 days from the beginning of the cycle have elapsed.

24. The method according to claim 1, wherein a treatment cycle is prolonged for a period until a WBC level in peripheral blood of 3,000/µl of blood or less reached, provided that the period does not exceed four weeks.

25. The method according to claim 23, wherein the amount of 15-deoxyspergulain or a pharmaceutically acceptable salt is reduced in the subsequent treatment cycle.

26. The method according to claim 1, wherein the amount of 15-deoxyspergualin or a pharmaceutical acceptable salt contained in the medicament is 0.01 mg to 100 mg/kg body weight of the patient.

27. The method according to claim 26, wherein the amount of 15-deoxyspergualin or a pharmaceutical acceptable salt is 0.01 mg to 5 mg/kg body weight of the patient.

28. The method according to claim 26, wherein the amount of 15-deoxyspergualin is 0.5 mg/kg/d.

29. The method according to claim 1, wherein the administration of the medicament to the patient is intravenous, intracutaneous, intraperitoneal, intrahecal, intraocular, ocular, buccal, nasal, percutaneous, cutaneous, topical, inhalative, intramuscular or rectal.

30. The method according to claim 1, wherein the patient is a human.

31. The method according to claim 1, wherein the patient is a monkey, dog, cat or rat.

32. The method according to claim 1, wherein the 15-deoxyspergulain or a pharmaceutically acceptable salt is a gusperimus hydrochloride.

* * * * *